US00PP10652P

United States Patent [19]

Welsh

[11] Patent Number: Plant 10,652

[45] Date of Patent: Oct. 20, 1998

[54] PEACH TREE DESIGNATED 'GW115'

[75] Inventor: W. Glenn Welsh, Martinsburg, W. Va.

[73] Assignee: Adams County Nursery, Inc., Aspers, Pa.

[21] Appl. No.: 800,555

[22] Filed: Feb. 18, 1997

[51] Int. Cl.[6] ..... A01H 5/00

[52] U.S. Cl. ..... Plt./43.1

[58] Field of Search ..... Plt./43.1

*Primary Examiner*—James R. Feyrer

*Attorney, Agent, or Firm*—John H. Vynalek; James A. Lucas

[57] ABSTRACT

A new and distinct variety of peach tree, designated GW115, originated as a seedling in a block of 'Loring'. It is an early season variety maturing before 'Redhaven'. The fruit is yellow fleshed, semi-freestone, firm, medium to large sized, aromatic and flavorful. The surface of the fruit is attractive red with a rich golden background.

2 Drawing Sheets

BACKGROUND OF THE DISCLOSURE

This invention relates to peach trees and, more specifically, to peach trees referred to as a variety of *Prunus persica* 'Batsch'.

I discovered this new and unique variety of peach tree as a seedling growing in a row of 'Loring' in a cultivated area near Martinsburg, W. Va. Although it is not known for certain, it is believed that this new variety of peach tree is an open pollinated seedling of 'Loring'. The tree of this invention produces a fruit of attractive commercial value, ripening after 'Garnet Beauty' and before 'Redhaven', a market period in which the industry lacks a peach of high quality.

This new variety of peach was asexually reproduced by grafting near Martinsburg, W. Va. and such reproduction has shown this new variety to come true in two successive generations. This propagation of the new variety by grafting under standard controlled conditions clearly discloses the continued maintenance of the characteristics described herein which distinguish this new variety from the parent variety and other related varieties of peach trees.

SUMMARY OF THE INVENTION

This new and distinctive variety of peach tree produces a fruit that is attractively colored, firm and uniformly shaped. It ripens prior to 'Redhaven' and after 'Garnet Beauty', two recognized standard, early season varieties in the Mid-Atlantic growing region. The fruit also has size, flavor and shelf life superior to 'Garnet Beauty', and exhibits a low incidence of split pit and shattered pit, which are serious disorders of early season varieties in general.

DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE PLANT

Figure 1:
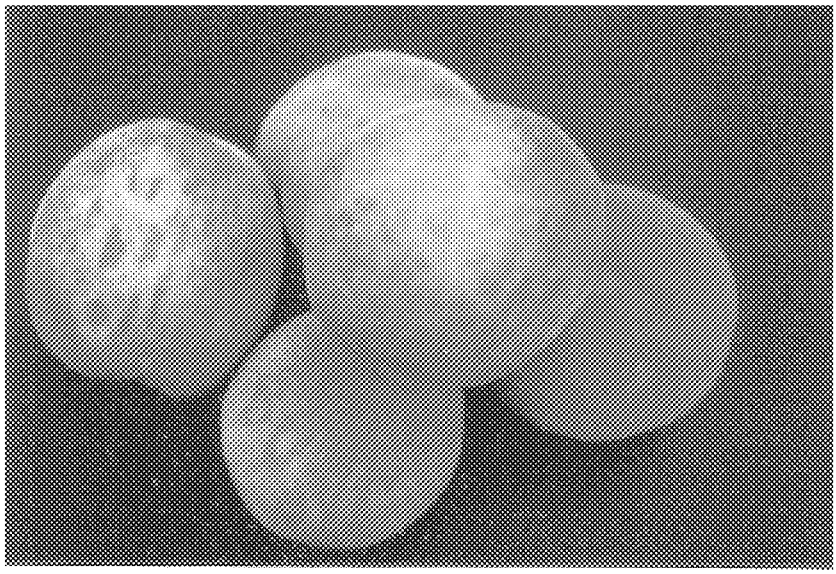
FIG. 1 is a close-up which depicts 5 specimens of fruit of the new tree in different orientations to reflect the uniform size, shape and characteristic mottled and blushed color patterns of the overcolor of the fruit over the contrasting ground color of the skin of the fruit. Also shown is the pistil point and suture of the fruit of this new tree.
Figure 2:
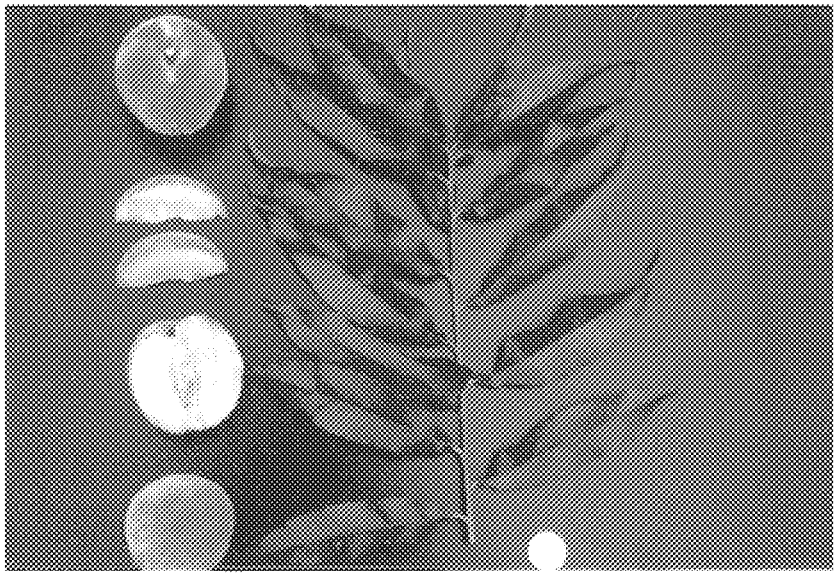
FIG. 2, depicts, at the top left, a whole specimen of the fruit shown from the stem end; at the middle left, a partially dissected fruit showing two slices and half of a fruit with stone; bottom left, a whole specimen of fruit from the apex; on the right a branch showing current season's growth showing the leaves, leaf arrangement and leaf spacing; and, a quarter placed to the right of the basal end of the stem to reflect the scale of the plant parts depicted.
Figure 3:
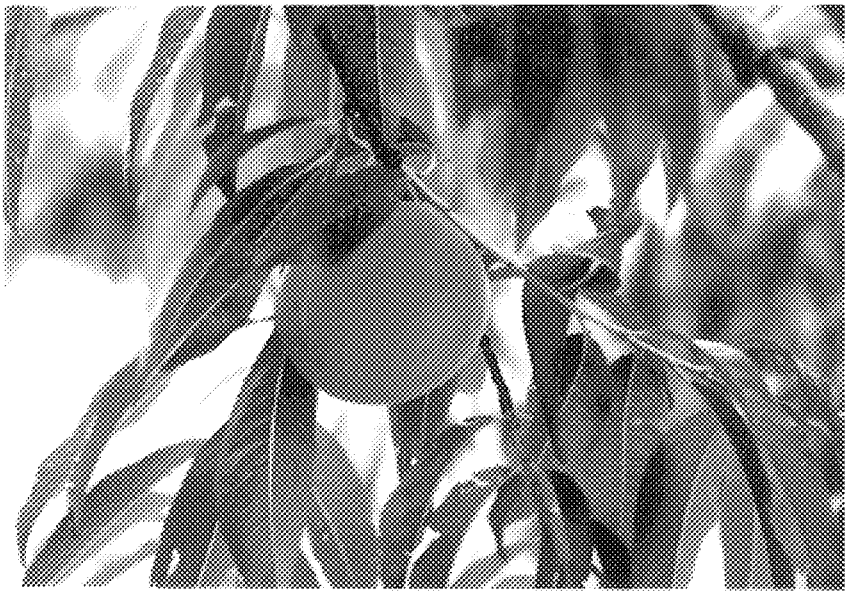
FIG. 3, shows a single specimen of fruit, at a stage of "harvest ripe" still attached to the tree. This photograph illustrates the strength of the bearing wood of the tree and the foliage top and bottom surfaces. Depicted also is the color of new stem bark as well as that of bearing wood from previous seasons.

All color references below are measured against The Royal Horticultural Society Colour Chart. Colors are approximate as color depends on horticultural practices such as light level and fertilization rate, among others.

Parentage:
- *Female parent.*—*Prunus persica* 'Loring'.
- *Pollen parent.*—Unknown.

Tree: Medium size, medium vigor, height and width (for a six year old tree grown near Aspers, Pa.)—7 feet by 8 feet.
- *Terminal shoot length.*—10 to 12 inches.
- *Canopy.*—Spreading, open center tree form, 60 degree branch angle at juncture with trunk.
- *Bearing.*—Medium productive, 1½ bushels (63 pounds) per tree in seventh leaf, annual bearer beginning in fourth leaf, half hardy, sensitivity to freeze damage similar to 'Loring'.
- *Trunk.*—Medium girth, medium smooth.
- *Branches.*—Medium girth, medium smooth, reddish gray, medium glossy.
- *Lenticels.*—Medium number, medium sized.

Leaves:
- *Length.*—6½ inches.
- *Width.*—1⅝ inches. Medium sized, lanceolate, pointed, thin, smooth.
- *Color.*—Medium green, R.H.S. 138B on top surface, R.H.S. 138D on bottom surface (from Royal Horticultural Society Colour Chart).
- *Margins.*—Finely serrate.

Petioles: Medium length, ⅝ inch, thick.
- *Glands of petiole.*—None, glandless.

Flowers:
- *Size.*—Medium, showy.
- *Bloom density.*—Medium.
- *Color.*—Rich pink, R.H.S. 65B.

*Dates of first and full blossoms.*—Apr. 19 and Apr. 23, 1996, (compared to April 21 and 25 for 'Redhaven') near Aspers, Pa.

*Flowering.*—Mid-season, blooms with 'Loring'.

*Pollination requirements.*—Self-fertile.

Fruit:

*Dates of first and last pickings.*—Jul. 22 and Jul. 29, 1996, (compared to July 27 and August 2 for 'Redhaven' and August 19 and August 25 for 'Loring') near Aspers, Pa.

*Days from peak bloom to "harvest ripe" stage.*—92.

*Number of pickings.*—3 or 4.

*Maturity when described.*—Firm-ripe.

*Size.*—Uniform, medium to large (large compared to other early season peaches).

*Axial diameter.*—2½ to 3 inches.

*Transverse in suture plane.*—8 to 9 inches circumference.

*At right angles to suture plane.*—8 to 9 inches circumference.

*Form.*—Uniform, symmetrical, globose slightly elongated on the suture plane.

*Suture.*—An inconspicuous line, has slight marked depression beyond pistil point.

*Ventral surface.*—Rounded, lips equal.

*Cavity.*—Rounded, suture showing on one side, depth 9/16 inch, breadth ½ inch, no markings.

*Base.*—Rounded.

*Apex.*—Rounded to truncate.

*Stem.*—Medium size, glabrous, medium adherence to stone.

*Skin.*—Medium thick, medium tender, free, no tendency to break.

*Color.*—Highly blushed (40 to 70% of surface) red, R.H.S. 45C, over yellow-orange background, R.H.S. 22C, mostly even with a few stripes or blotches.

*Down.*—Moderate, short.

*Flesh.*—Yellow color, R.H.S. 10C, occasional red streaks.

*Surface of pit cavity.*—Yellow, R.H.S. 10C.

*Texture.*—Firm, about 40N at harvest.

*Fibres.*—Few, fine.

*Ripens.*—Fairly even.

*Flavor.*—Excellent sweet/sour balance, about 10% soluble solids, about 0.80% titratable acidity.

*Aroma.*—Distinct.

Eating quality: Good to best.

Stone: Semi-free (free when fully ripe).

*Color.*—Tan, R.H.S. 161D.

*Fibres.*—Part from flesh smoothly.

*Size.*—Medium.

*Length.*—1½ inch.

*Thickness.*—¾ inch.

*Form.*—Oblong.

*Base.*—Oblique.

*Hilum.*—Narrow.

*Apex.*—Acute.

*Sides.*—Equal.

*Surface.*—Irregularly furrowed throughout, pitted throughout.

*Ridges.*—Rounded toward apex.

*Pits.*—Circular, elongated.

*Dorsal edge.*—Narrow with shallow groove.

Uses: Local, dessert and culinary markets.

Keeping quality: Excellent. Can be stored until beginning of 'Loring' season.

Resistance to insects: Medium.

Resistance to diseases: Medium, no bacterial spot.

Shipping quality: Good to excellent.

I claim:

1. A new distinct variety of peach tree, as illustrated and described, characterized by fruit of early maturity, attractive color, firm flesh, long shelf-life and low incidence of split or shattered pits.

* * * * *